US012071965B2

(12) United States Patent
Wu et al.

(10) Patent No.: US 12,071,965 B2
(45) Date of Patent: Aug. 27, 2024

(54) ELECTRONIC CIGARETTE AND ATOMIZER THEREOF

(71) Applicant: SHENZHEN SMOORE TECHNOLOGY LIMITED, Shenzhen (CN)

(72) Inventors: Zhenyu Wu, Shenzhen (CN); Wenli Du, Shenzhen (CN); Gaoren Yao, Shenzhen (CN)

(73) Assignee: SHENZHEN SMOORE TECHNOLOGY LIMITED, Shenzhen (CN)

( * ) Notice: Subject to any disclaimer, the term of this patent is extended or adjusted under 35 U.S.C. 154(b) by 700 days.

(21) Appl. No.: 16/595,511

(22) Filed: Oct. 8, 2019

(65) Prior Publication Data
US 2020/0107583 A1    Apr. 9, 2020

(30) Foreign Application Priority Data

Oct. 8, 2018    (CN) .......................... 201821630910.8

(51) Int. Cl.
*A24F 40/10*    (2020.01)
*A24F 40/40*    (2020.01)
(Continued)

(52) U.S. Cl.
CPC ................ *F16B 1/00* (2013.01); *A24F 47/00* (2013.01); *A61M 15/06* (2013.01); *A24F 40/10* (2020.01);
(Continued)

(58) Field of Classification Search
CPC .................................. A24F 40/10; A24F 40/40
(Continued)

(56) References Cited

U.S. PATENT DOCUMENTS 4,882,203 A   11/1989   Witmer
9,032,968 B2 *  5/2015   Glasberg ................. A24F 40/90
                                                 131/273
(Continued)

FOREIGN PATENT DOCUMENTS

CN       104000306       8/2014
CN       108185536       6/2018
(Continued)

OTHER PUBLICATIONS

Machine Translation of CN 108185536 (Year: 2018).*
(Continued)

*Primary Examiner* — Russell E Sparks
(74) *Attorney, Agent, or Firm* — JCIP GLOBAL INC.

(57) ABSTRACT

An atomizer comprises an atomizing body, an atomizing base disposed at one end of the atomizing body, and a fixing member installed outside the atomizing base and connected with the atomizing body. The atomizing base is fixed on the atomizing body by the fixing member, and the fixing member is made of a material that can be adsorbed by a magnet and comprises a tabular main body portion corresponding to the atomizing base. The atomizing base is fixed on the atomizing body by the fixing member, and after the atomizer is connected and assembled with a power supply assembly, an adsorption force between the tabular main body portion and the magnet can increase.

11 Claims, 4 Drawing Sheets

(51) Int. Cl.
*A24F 47/00* (2020.01)
*A61M 15/06* (2006.01)
*F16B 1/00* (2006.01)
*A61M 11/04* (2006.01)
*A61M 15/08* (2006.01)

(52) U.S. Cl.
CPC ............ *A24F 40/40* (2020.01); *A61M 11/042* (2014.02); *A61M 15/085* (2014.02); *F16B 2200/83* (2023.08)

(58) Field of Classification Search
USPC ........................................................ 131/329
See application file for complete search history.

(56) References Cited

U.S. PATENT DOCUMENTS

| | | | | |
|---|---|---|---|---|
| 9,402,421 | B2* | 8/2016 | Liu | A24F 40/40 |
| 11,470,880 | B2* | 10/2022 | Ouyang | A61M 15/06 |
| 11,903,419 | B2* | 2/2024 | Li | H05B 1/0297 |
| 2015/0305409 | A1* | 10/2015 | Verleur | A24F 40/40 |
| | | | | 131/329 |
| 2016/0007654 | A1* | 1/2016 | Zhu | A24F 40/42 |
| | | | | 131/328 |
| 2019/0099562 | A1* | 4/2019 | Nettenstrom | A24F 40/485 |
| 2021/0059308 | A1* | 3/2021 | Lin | A24F 40/42 |
| 2022/0007728 | A1* | 1/2022 | Wu | A24F 40/40 |

FOREIGN PATENT DOCUMENTS

| | | | |
|---|---|---|---|
| CN | 108354235 | 8/2018 | |
| CN | 108451038 | 8/2018 | |
| EP | 2875740 | 5/2015 | |
| WO | 2017163045 | 9/2017 | |
| WO | WO-2019157651 A1 * | 8/2019 | A24F 40/44 |
| WO | 2019218122 | 11/2019 | |

OTHER PUBLICATIONS

"Search Report of Europe Counterpart Application", issued on Dec. 3, 2019 p. 1-p. 6.
"Office Action of European Related Application No. 19200536.1", issued on Jun. 30, 2022, pp. 1-5.

* cited by examiner

ELECTRONIC CIGARETTE AND ATOMIZER THEREOF

CROSS-REFERENCE TO RELATED APPLICATION

This application claims the priority benefit of China application serial no. 201821630910.8, filed on Oct. 8, 2018. The entirety of the above-mentioned patent application is hereby incorporated by reference herein and made a part of this specification.

BACKGROUND

Technical Field

The present invention relates to the field of cigarette substitutes, in particular to an electronic cigarette and an atomizer thereof.

Description of Related Art

Electronic cigarettes are also known as virtual cigarettes or electronic atomizers. As alternative cigarette products, electronic cigarettes are usually used to quit smoking. Electronic cigarettes have similar appearance and taste to cigarettes, but generally do not contain other harmful components such as tar and particulate matter in cigarettes.

Each electronic cigarette consists essentially of an atomizer and a power supply assembly. At present, the atomizer of the electronic cigarette mostly comprises a fiber rope for guiding liquid and a heating wire wound around the fiber rope. As both the fiber rope and the heating wire are made of flexible materials, installing and fixing structures thereof are relatively complicated.

The atomizer is usually in magnetic connection with the power supply assembly. In order to ensure adsorption, an atomizing base of the atomizer and an end of the power supply assembly are respectively provided with at least one magnet, the at least one magnet at the two corresponding ends magnetically adsorb the atomizer and the power supply assembly together. The use of the magnets at both ends can increase the cost of the electronic cigarette, and also makes assembling more cumbersome.

In addition, the atomizing base is usually made of a plastic or silica gel material. During a heating process of the electronic cigarette, deformation will occur due to thermal expansion and cold shrinkage, thereby causing looseness between components, and causing the atomizer to bulge and affect the sealing effect.

SUMMARY

The technical problem to be solved by the present invention is to provide an improved electronic cigarette and an atomizer thereof.

The technical solution adopted by the present invention to solve the technical problem thereof is to construct an atomizer comprising an atomizing body, an atomizing base disposed at one end of the atomizing body, and a fixing member installed outside the atomizing base and connected with the atomizing body. The atomizing base is fixed on the atomizing body by the fixing member, and the fixing member is made of a material that can be adsorbed by a magnet and comprises a tabular main body portion corresponding to the atomizing base.

Preferably, the atomizing base is provided with at least one electrode, and an evading hole is disposed proximate to the at least one electrode on the main body portion to expose the at least one electrode.

Preferably, the atomizing base is further provided with a vent hole, and the evading hole is proximate to the vent hole to expose the vent hole.

Preferably, a liquid storage chamber and an airflow passage are formed in the atomizing body, and one end of the atomizing body is provided with a liquid injection opening for injecting aerosol-generating substrate into the liquid storage chamber. The atomizer comprises a sealing assembly sealed on the liquid injection opening, and an atomizing assembly disposed on the other side of the sealing assembly beyond the liquid storage chamber. The atomizing assembly is disposed between the atomizing base and the sealing assembly, and respectively communicated with the airflow passage and the vent hole, and the at least one electrode is conducted with the atomizing assembly. The sealing assembly is provided with at least one liquid outlet communicated with the liquid storage chamber, and the atomizing assembly comprising a liquid absorbing member for absorbing the aerosol-generating substrate flowing out from the at least one liquid outlet, and a heating member for heating and atomizing the aerosol-generating substrate on the liquid absorbing member.

Preferably, the fixing member is made of a metal material that can be adsorbed by the magnet.

Preferably, the fixing member further comprises a connecting portion disposed from an outer edge of the main body portion to one side of the atomizing body, and the connecting portion is fixedly connected with the atomizing body for positioning.

Preferably, the connecting portion is tubular and is sleeved on the atomizing body.

Preferably, an outside surface of the atomizing body is buckled with the connecting portion to prevent disengagement.

Preferably, the outside surface of the atomizing body is provided with a buckle, and the connecting portion is provided with a buckling hole buckled with the buckle.

An electronic cigarette comprises the atomizer and a power supply assembly detachably connected with the atomizer. The power supply assembly comprises a receptacle connected with an end where the fixing member is positioned, and the receptacle is provided with at least one magnet corresponding to the main body portion.

By implementing the electronic cigarette and the atomizer thereof of the present invention, the following beneficial effects can be achieved. The atomizing base is fixed on the atomizing body by the fixing member, and after the atomizer is connected and assembled with the power supply assembly, an adsorption force between the tabular main body portion and the magnet can increase. As an area of the fixing member corresponding to the power supply assembly is large enough, the adsorption force between the fixing member and the magnet on the power supply assembly is strong enough, so that it is not necessary to provide the atomizer with the magnet, and thus the cost can be reduced.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated

DESCRIPTION OF THE EMBODIMENTS

For a better understanding of the technical features, objects and effects of the present invention, the embodiments of the present invention will be described in detail with reference to the accompanying drawings.

Figure 1:
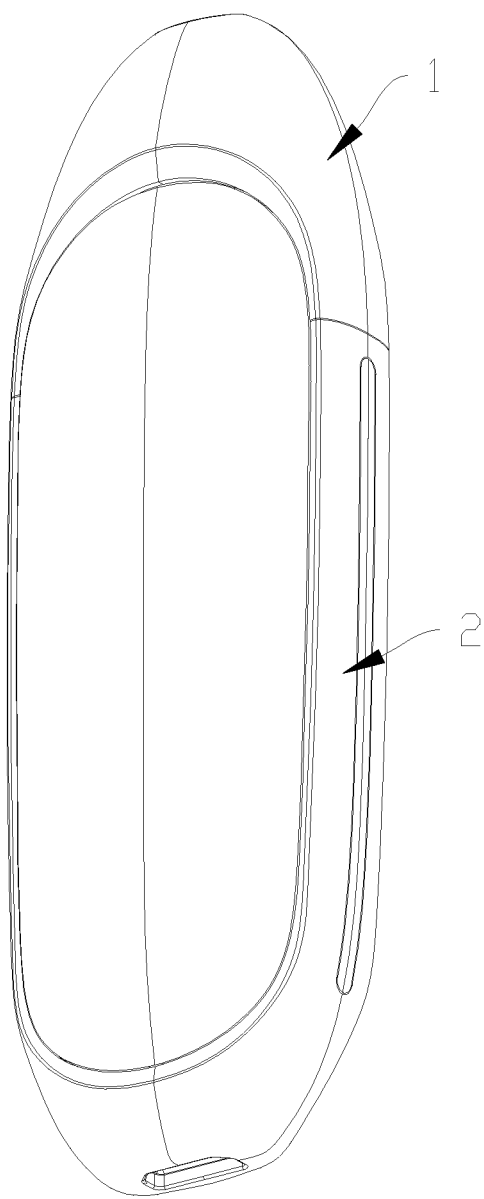
FIG. 1 is a schematic diagram of a three-dimensional structure of an electronic cigarette in an example of the present invention.
Figure 2:
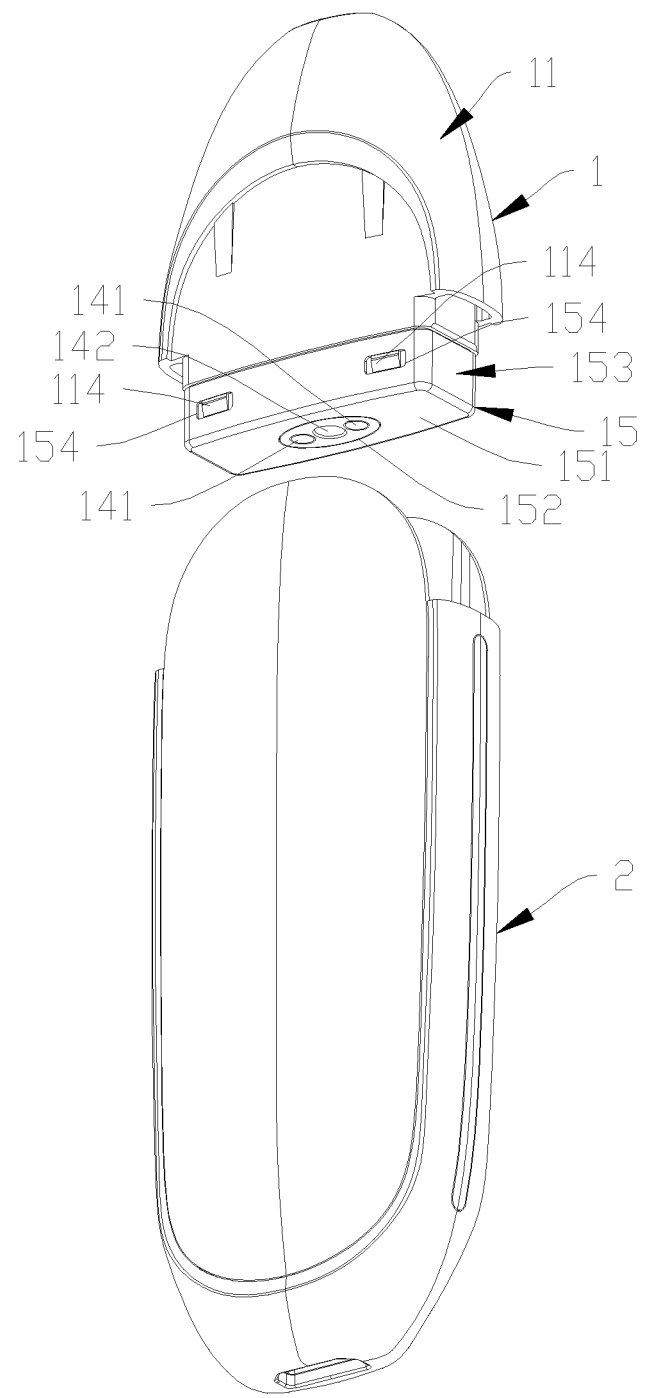
FIG. 2 is a schematic structural diagram of an atomizer and a power supply assembly of the electronic cigarette in FIG. 1 after being disassembled.

As shown in FIG. 1 and FIG. 2, an electronic cigarette in a preferred example of the present invention comprises an atomizer 1, and a power supply assembly 2 detachably connected with the atomizer 1, and when the atomizer 1 is connected with the power supply assembly 2, the power supply assembly 2 supplies power to the atomizer 1 to enable an atomizing assembly 13 in the atomizer 1 to generate heat for heating and atomizing aerosol-generating substrate (usually a liquid).

Figure 3:
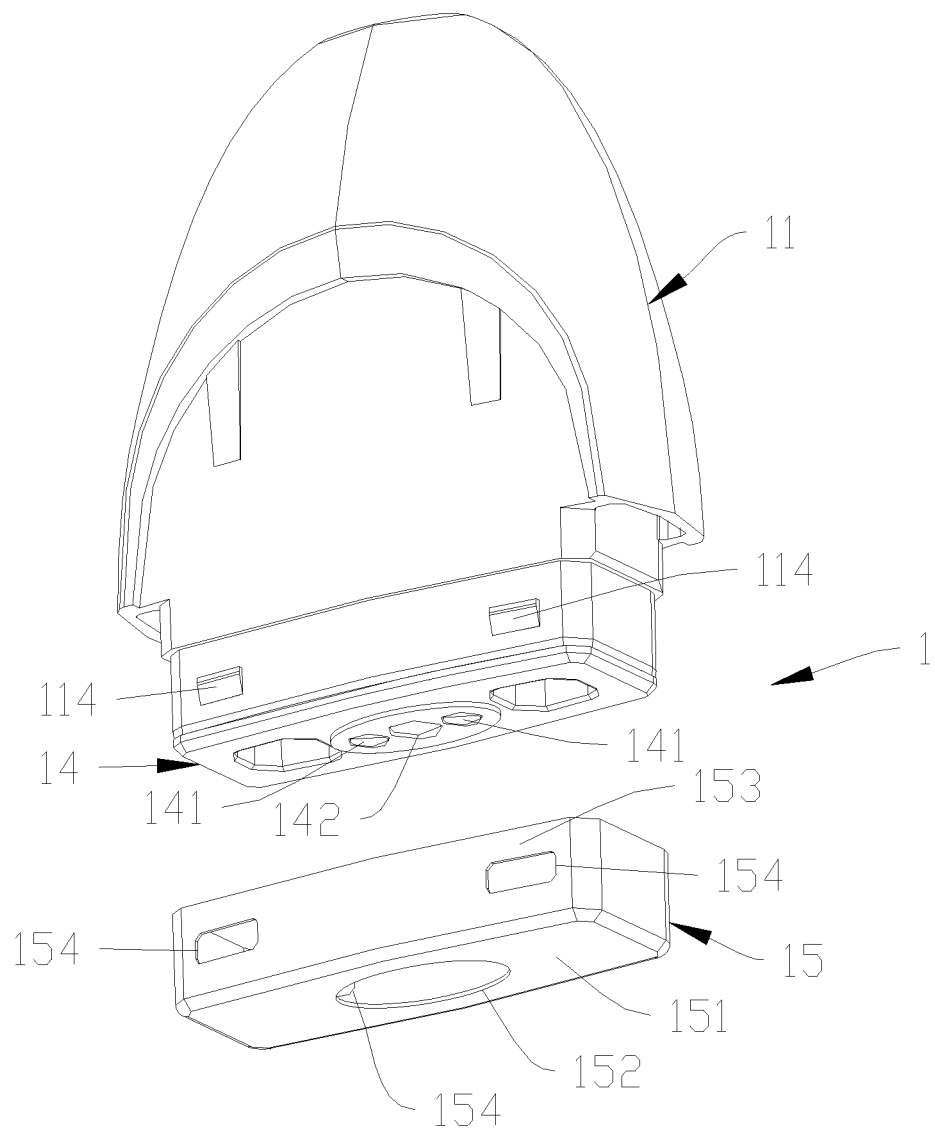
FIG. 3 is a schematic structural diagram of a fixing member and an atomizing body of the atomizer in FIG. 2 after being separated.
Figure 4:
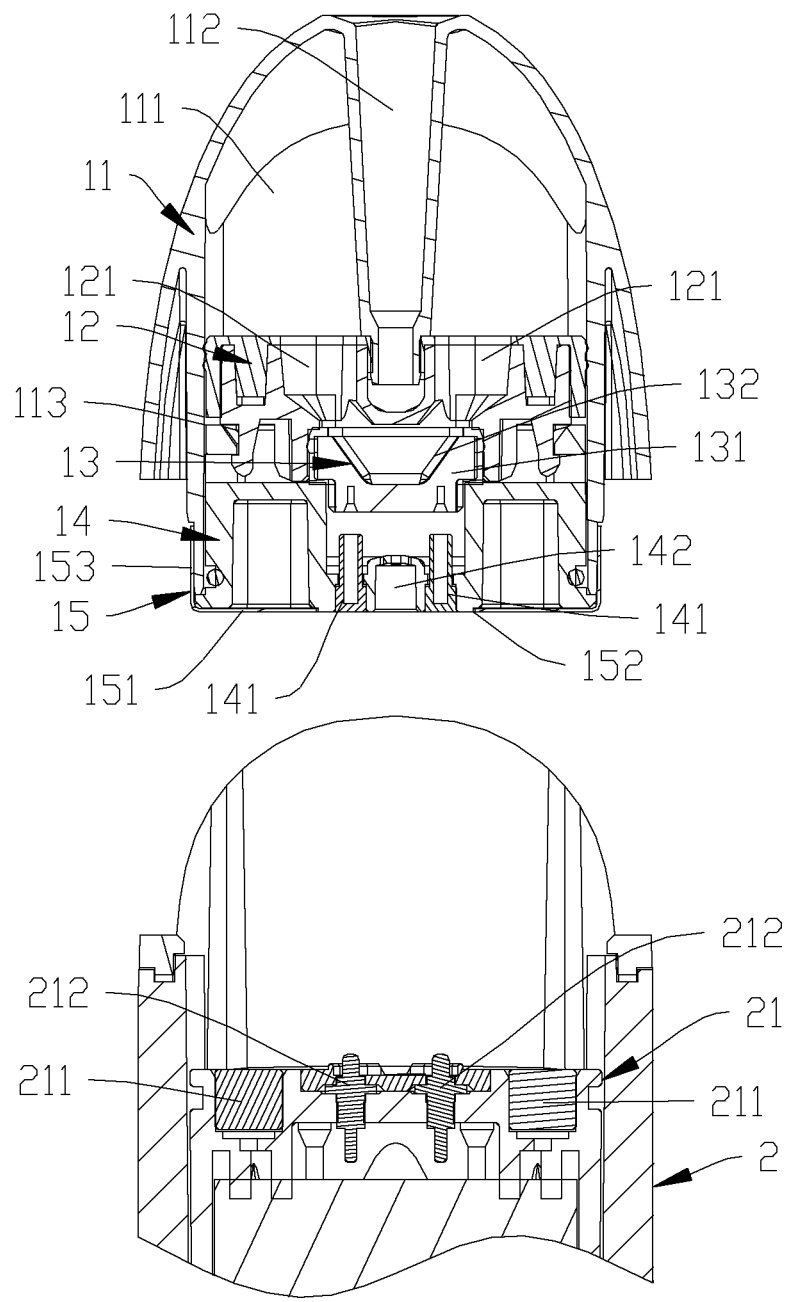
FIG. 4 is a schematic cross-sectional diagram of the atomizer and the power supply assembly in FIG. 2 after being disassembled.

As shown in FIG. 2 to FIG. 4, the atomizer 1 comprises an atomizing body 11, a sealing assembly 12, an atomizing assembly 13, an atomizing base 14, and a fixing member 15. A liquid storage chamber 111 and an airflow passage 112 are formed in the atomizing body 11, and one end of the atomizing body 11 is provided with a liquid injection opening 113 for injecting aerosol-generating substrate into the liquid storage chamber 111.

The sealing assembly 12 is sealed on the liquid injection opening 113, and the atomizing assembly 13 is disposed on the other side of the sealing assembly 12 beyond the liquid storage chamber 111. The sealing assembly 12 is provided with at least one liquid outlet 121 communicated with the liquid storage chamber 111 to enable the aerosol-generating substrate in the liquid storage chamber 111 to flow out and onto the atomizing assembly 13 to be heated and atomized.

The atomizing assembly 13 comprises a liquid absorbing member 131 for absorbing the aerosol-generating substrate flowing out from the at least one liquid outlet 121, and a heating member 132 for heating and atomizing the aerosol-generating substrate on the liquid absorbing member 131. The liquid absorbing member 131 may be a component such as a liquid absorbing cotton or liquid absorbing ceramic, and the heating member 132 may be a heating wire or a heating track.

The atomizing base 14 is disposed at one end corresponding to the liquid injection opening 113 of the atomizing body 11 to enable the atomizing assembly 13 to be disposed between the atomizing base 14 and the sealing assembly 12, so that positions of the sealing assembly 12 and the atomizing base 14 can be maintained to be stable.

The atomizing base 14 is provided with at least one electrode 141 and a vent hole 142, and the at least one electrode 141 is conducted with the heating member 132 of the atomizing assembly 13 to enable the power supply assembly 2 to be conducted with the at least one electrode 141 for supplying power to the heating member 132. The vent hole 142, the atomizing assembly 13, and the airflow passage 112 are communicated with one another, so that when a user draws, an environment gas can enter the atomizer 1 through the vent hole 142, and bring an aerosol generated by the atomizing assembly 13 after heating and atomizing the aerosol-generating substrate to a suction nozzle through the airflow passage 112 and enter the mouth of the user.

The fixing member 15 is installed outside the atomizing base 14 and connected with the atomizing body 11, so that the atomizing base 14 is fixed on the atomizing body 11 to prevent the atomizing base 14 from falling off. The fixing member 15 is made of a material that can be adsorbed by a magnet 211 and comprises a tabular main body portion 151 corresponding to the atomizing base 14.

An evading hole 152 is disposed proximate to the at least one electrode 141 on the main body portion 151 to expose the at least one electrode 141. In addition, the evading hole 152 is proximate to the vent hole 142 to expose the vent hole 142. In other examples, the at least one electrode 141 and the vent hole 142 may also be disposed on other side surfaces of the atomizing base 14, so that after the atomizer 1 is assembled with the power supply assembly 2, electrical conduction and ventilation are achieved.

The power supply assembly 2 comprises a receptacle 21 connected with an end where the fixing member 15 is positioned, and the receptacle 21 is provided with at least one magnet 211 corresponding to the main body portion 151 and at least one conductive elastic pin 212 corresponding to the at least one electrode 141, the at least one magnet 211 may be fixed with the main body portion 151 through adsorption, the at least one conductive elastic pin 212 may be conducted with the at least one electrode 141 for supplying power to the atomizer 1. A number of the magnet 211 at the receptacle 21 is two, which can ensure that the position after adsorption is stable. In other examples, the number of the magnet 211 may also be one or other numbers larger than two.

The atomizing base 14 is fixed on the atomizing body 11 by the fixing member 15, and after the atomizer 1 is connected and assembled with the power supply assembly 2, an adsorption force between the tabular main body portion 151 and the at least one magnet 211 can increase. As an area of the fixing member 15 corresponding to the power supply assembly 2 is large enough, the adsorption force between the fixing member 15 and the at least one magnet 211 on the power supply assembly 2 is strong enough, so that it is not necessary to provide the atomizer 1 with the magnet 211, and thus the cost can be reduced.

The fixing member 15 is made of a metal material that can be adsorbed by the magnet 211, such as stainless steel materials with brands of SPCC, SECC, SGCC, SPHC, SPTE and the like, and then may be integrally molded by adopting a stamping process, which makes a manufacturing process simpler. In other examples, the fixing member 15 may also be other magnetic member that can be adsorbed by the magnet 211 after being magnetized.

In addition, as a bottom portion of the atomizer 1 is fixed by the fixing member 15, and the fixing member 15 is made of the metal material, thermal expansion and cold shrinkage can be reduced caused by temperature changes during a heating process, so that fixing among all the components of the atomizer 1 are more stable and reliable, and the sealing property is better.

In some examples, in order to better fixedly connect the fixing member 15 with the atomizing base 14, and also to simplify the assembling process, the fixing member 15 further comprises a connecting portion 153 disposed from an outer edge of the main body portion 151 to one side of the atomizing body 11, and the connecting portion 153 is fixedly connected with the atomizing body 11 for positioning.

Preferably, the connecting portion 153 is tubular and is sleeved on the atomizing body 11. Further, an outside surface of the atomizing body 11 is buckled with the connecting portion 153 to prevent disengagement. In this example, the outside surface of the atomizing body 11 is provided with a buckle 114, and the connecting portion 153 is provided with a buckling hole 154 buckled with the buckle 114.

In other examples, the connecting portion 153 may also be fixed to the atomizing base 14 directly by means of a sleeving force during sleeving, or the connecting portion 153 may also be elastically clamped to an outside surface of the atomizing base 14 through an elastic structure such as an elastic arm.

It will be understood that the various technical features above may be used in any combination without limitation.

The description above is only examples of the present invention, and thus does not limit the scope of the patent of the present invention. Any equivalent structure or equivalent flow transformation made by using the description and the drawings of the present invention, or directly or indirectly applied to other related technical fields, should be similarly included in the protection scope of the patent of the present invention.

What is claimed is:

1. An atomizer, comprising:
an atomizing body, wherein a liquid storage chamber and an airflow passage are formed in the atomizing body, and one end of the atomizing body is provided with a liquid injection opening for injecting aerosol-generating substrate into the liquid storage chamber;
an atomizing base disposed at one end of the atomizing body, wherein at least one electrode and a vent hole are disposed on a bottom surface of the atomizing base;
a fixing member disposed outside the atomizing base and connected with the atomizing body to fix the atomizing base with the atomizing body, wherein the fixing member is made of a magnetic metal material, the fixing member comprises a tabular main body portion corresponding to the atomizing base, the tabular main body portion covers the bottom surface of the atomizing base, an evading hole is formed in the tabular main body portion to completely expose both of the at least one electrode and the vent hole, and the vent hole and the evading hole are disposed along a central axis of the atomizer;
a sealing assembly sealed on the liquid injection opening; and
an atomizing assembly, wherein the liquid storage chamber, the sealing assembly, and the atomizing assembly are disposed along a direction of an extension of the airflow passage in sequence.

2. The atomizer according to claim 1, wherein
the atomizing assembly is disposed between the atomizing base and the sealing assembly, and respectively communicated with the airflow passage and the vent hole, and the at least one electrode is conducted with the atomizing assembly; and
the sealing assembly is provided with at least one liquid outlet communicated with the liquid storage chamber, and the atomizing assembly includes a liquid absorbing member for absorbing the aerosol-generating substrate flowing out from the at least one liquid outlet, and a heating member for heating and atomizing the aerosol-generating substrate on the liquid absorbing member.

3. The atomizer according to claim 1, wherein the fixing member further comprises a connecting portion disposed from an outer edge of the tabular main body portion to one side of the atomizing body, and the connecting portion is fixedly connected with the atomizing body for positioning.

4. The atomizer according to claim 3, wherein the connecting portion is rectangular and is sleeved on the atomizing body.

5. The atomizer according to claim 3, wherein an outside surface of the atomizing body is buckled with the connecting portion to prevent disengagement.

6. The atomizer according to claim 5, wherein the outside surface of the atomizing body is provided with a buckle, and the connecting portion is provided with a buckling hole buckled with the buckle.

7. An electronic cigarette, comprising the atomizer according to claim 1, and a power supply assembly detachably connected with the atomizer, wherein the power supply assembly comprises a receptacle connected with an end where the fixing member is positioned, and the receptacle is provided with at least one magnet corresponding to the tabular main body portion.

8. The electronic cigarette according to claim 7, wherein
the atomizing assembly is disposed between the atomizing base and the sealing assembly, and respectively communicated with the airflow passage and the vent hole, and the at least one electrode is conducted with the atomizing assembly; and
the sealing assembly is provided with at least one liquid outlet communicated with the liquid storage chamber, and the atomizing assembly includes a liquid absorbing member for absorbing the aerosol-generating substrate flowing out from the at least one liquid outlet, and a heating member for heating and atomizing the aerosol-generating substrate on the liquid absorbing member.

9. The electronic cigarette according to claim 7, wherein the fixing member further comprises a connecting portion disposed from an outer edge of the tabular main body portion to one side of the atomizing body, and the connecting portion is fixedly connected with the atomizing body for positioning.

10. The electronic cigarette according to claim 9, wherein the connecting portion is rectangular and is sleeved on the atomizing body.

11. The electronic cigarette according to claim 9, wherein an outside surface of the atomizing body is buckled with the connecting portion to prevent disengagement.

* * * * *